US012644875B2

(12) United States Patent
Shire

(10) Patent No.: US 12,644,875 B2
(45) Date of Patent: Jun. 2, 2026

(54) COORDINATION OF SENSORS IN PROXIMITY

(71) Applicant: VOLVO TRUCK CORPORATION, Gothenburg (SE)

(72) Inventor: Joshua Shire, Gothenburg (SE)

(73) Assignee: VOLVO TRUCK CORPORATION, Gothenburg (SE)

( * ) Notice: Subject to any disclaimer, the term of this patent is extended or adjusted under 35 U.S.C. 154(b) by 617 days.

(21) Appl. No.: 18/002,985

(22) PCT Filed: Jun. 24, 2020

(86) PCT No.: PCT/EP2020/067700
§ 371 (c)(1),
(2) Date: Dec. 22, 2022

(87) PCT Pub. No.: WO2021/259468
PCT Pub. Date: Dec. 30, 2021

(65) Prior Publication Data
US 2023/0333073 A1 Oct. 19, 2023

(51) Int. Cl.
*G01N 33/00* (2006.01)
(52) U.S. Cl.
CPC ................................. *G01N 33/0075* (2013.01)
(58) Field of Classification Search
CPC .................................................. G01N 33/0075
See application file for complete search history.

(56) References Cited

U.S. PATENT DOCUMENTS

| | | | | |
|---|---|---|---|---|
| 6,687,571 | B1 * | 2/2004 | Byrne | .................. G05D 1/0289 |
| | | | | 700/39 |
| 8,131,839 | B2 | 3/2012 | Yu et al. | |
| 2004/0030451 | A1 * | 2/2004 | Solomon | ............ H04B 7/18517 |
| | | | | 73/178 R |
| 2009/0037570 | A1 * | 2/2009 | Yu | ........................... G01D 21/00 |
| | | | | 709/224 |
| 2009/0055691 | A1 * | 2/2009 | Ouksel | .................. H04W 64/00 |
| | | | | 714/48 |
| 2015/0059444 | A1 | 3/2015 | Rella | |

(Continued)

FOREIGN PATENT DOCUMENTS

| | | |
|---|---|---|
| JP | 2018017586 A | 2/2018 |
| WO | 2018193205 A1 | 10/2018 |

OTHER PUBLICATIONS

International Search Report and Written Opinion of the International Searching Authority in corresponding International Application No. PCT/EP2020/067700 mailed Feb. 22, 2021 (15 pages).

(Continued)

*Primary Examiner* — Jelani A Smith
*Assistant Examiner* — Khabeer Salaam
(74) *Attorney, Agent, or Firm* — Jeffri A. Kaminski; Venable LLP

(57) ABSTRACT

A method of coordinating sampling instants of a plurality of mobile ambient sensors, comprising: receiving a definition of a measuring zone; detecting simultaneous presence of two or more mobile ambient sensors in the measuring zone; and assigning sampling instants to each of said two or more sensors, wherein the assigned sampling instants apply until a change in said simultaneous presence is detected.

15 Claims, 5 Drawing Sheets

(56) References Cited

U.S. PATENT DOCUMENTS

| | | | | |
|---|---|---|---|---|
| 2017/0284839 | A1 | 10/2017 | Ojala | |
| 2018/0316764 | A1* | 11/2018 | Ferreira Gomes | G07C 5/02 |
| 2019/0068434 | A1* | 2/2019 | Moreira da Mota | H04W 88/10 |
| 2019/0208018 | A1* | 7/2019 | Scanlin | H04L 67/125 |
| 2020/0132650 | A1* | 4/2020 | Zanini | G06T 17/20 |

OTHER PUBLICATIONS

Srinivas Devarakonda et al; "Real-time Air Quality Monitoring Through Mobile Sensing in Metropolitan Areas"; UrbComp '13: Proceedings of the 2nd ACM SIGKDD International Workshop on Urban Computing; Aug. 2013; Article No. 15; pp. 1-8; https://doi.org/10.1145/2505821.2505834 (8 pages).

Pedro Henrique Cruz Caminha et al; "On the Coverage of Bus-Based Mobile Sensing"; Sensors (Basel). Jun. 2018;18(6): 1976; Published online: Jun. 20, 2018; doi: 10.3390/s18061976; 12 pages.

\* cited by examiner

*100* receive definition of the measuring zone — *110* receive sampling periodicity — *112* detect sensors present — *114* receive scheduled routes — *116* assign sampling instants — *118*

COORDINATION OF SENSORS IN PROXIMITY

CROSS-REFERENCE TO RELATED APPLICATIONS

This application is a U.S. National Stage application of PCT/EP2020/067700, filed Jun. 24, 2020 and published on Dec. 30, 2021, as WO 2021/259468, all of which is hereby incorporated by reference in its entirety.

TECHNICAL FIELD

The present disclosure relates to the field of mobile measurements and in particular to the scheduling of time instants for sampling using moving sensors, such as ambient sensors carried by vehicles.

BACKGROUND

Air quality, radio conditions and other location-dependent quantities are traditionally measured using equipment fixedly installed at specific locations or by operating mobile laboratories. These are expensive yet coarse-grained approaches, where the measurements tend to be few and widely spaced apart. Recent attention has been given to mobile measuring techniques using vehicles already moving around an urban environment, where air quality is analyzed in real time and with low spatial granularity.

As one example, Devarakonda et al., "Real-Time Air Quality Monitoring Through Mobile Sensing in Metropolitan Areas", *Proceedings of UrbComp'* 13 (2013) discloses air pollution sampling using public transportation vehicles and discusses sampling strategies. Further, Cruz Caminha et al., "On the Coverage of Bus-Based Mobile Sensing", Sensors, vol. 2018, issue 18, no 1976 (2018) discloses air pollution sampling using buses equipped with air pollution sensors, and discusses the balance between coverage and sensing frequency for a fleet of buses having such sensors.

The proposals by Devarakonda and Cruz Caminha both use sensors configured to measure periodically, such as twice an hour. Because the sensors are unsynchronized, both in regard to each other and to a common time base, it must be accepted that the sampling may occur anytime (in clock time) during a data collection session. This may lead to inconvenient clustering or sparseness of the samples in a given measuring area. In other words, the spatial and/or temporal coverage of the data points may be less comprehensive than their number suggests. Deficient coverage may to some extent be remedied by extending the measuring period, which however ties up the equipment unnecessarily and inflates the data set to be processed.

WO2018193205 presents an algorithm for assigning measuring locations on trajectories along which mobile sensors travel in an observation zone. More precisely, the algorithm finds a "spatial distribution" $S_{opt}$, representing the sensor position at the common sampling instant, that approximates the observation zone optimally.

There is a need for more intelligent coordination of nearby mobile sensors.

SUMMARY

One objective is to make available methods and devices for controlling sampling at a plurality of mobile ambient sensors which move into and out of each other's proximity.

A further objective is to address inherent limitations of the sensors, such as refractory periods.

These and other objectives are achieved by the invention defined by the independent claims. The dependent claims relate to embodiments of the invention.

One aspect of the invention relates to a method of controlling sampling at a plurality of mobile ambient sensors. An early step of the method is to receive a definition of a measuring zone. As used herein, a "measuring zone" has such size that two measurements in the zone, from the point of view of their beneficiary, are mutually substitutable. The measuring zone may be defined by the beneficiary or an administrator; it may be considered to relate to a single location. According to the method, further, when two or more mobile ambient sensors are simultaneously present in the measuring zone, sampling instants are assigned to each of these. The sampling instants apply until there is a change in the simultaneous presence.

This method allows precise coordination of multiple sensors. The clustering effect seen in the state-of-the-art measuring techniques can be easily avoided. Because the measurements by the different mobile ambient sensors are mutually substitutable within the measuring zone, the method may serve to distribute the workload between the sensors by assigning the sampling instants accordingly. The fact that the assigned sampling instants apply (e.g., in the sense of being exe-cutable by the mobile ambient sensors) up to a next change in simultaneous presence (e.g., a sensor leaves or enters the measuring zone, a sensor goes defective and thereby functionally becomes a non-sensor) economizes the computational effort.

In one embodiment, the method includes the detection of a change in simultaneous presence. The detection may be based on a relative positioning procedure which the sensors performs among themselves, such as by transmitting and detecting radio-frequency signals, including ranging signals, discovery signals, LTE sidelink as well as network-supported positioning. Alternatively or additionally, the detection may be based on a geolocation procedure performed at one of the sensors, i.e., by the sensor itself or by a vehicle or vessel on which the sensor is mounted. Further alternatively or additionally, the entity executing the method may determine the change in simultaneous presence by receiving a report from a roadside transceiver or other cellular or non-cellular network equipment which is configured to determine a position of at least one of the mobile ambient sensors. Further alternatively or additionally, the entity executing the method may determine the change in simultaneous presence by non-receipt of an expected measurement report; this may signify that the sensor concerned has moved out of a coverage area of a transceiver to which it is configured to deliver its measurement data. The mentioned approaches may also be applied conversely in order to determine the appearance of a new mobile ambient sensor in the measuring zone. In response to a change in the simultaneous presence—or a predetermined number of such changes—the method may loop to the step of assigning sampling instants, which may now be repeated in view of the current set of sensors present in the measuring zone.

In one embodiment, the sampling instances are periodic sampling instants. As an example, rather than assigning the sampling instances one by one, the method may determine a sampling periodicity that is to elapse before the next sample. The desired phase of each sensor's sampling may be expressed as an explicit starting time in terms of a time base or it may be implicit from the moment of transmitting the sampling periodicity to the sensor concerned or a time at which it is received by the sensor. The second signaling format consumes less bandwidth and does not require reliable synchronization with respect to the time base, but it may on the other hand be somewhat less accurate. With either signaling format, the use of a sampling periodicity may be a convenient and data-economical way of instructing the ambient sensors about the sampling instants, particularly so if the validity of the sampling instant assignment is at least a few multiples of the sampling periodicity.

In one embodiment, the assignment of sampling instants is assisted by information about a scheduled route of one of the simultaneously present sensors. The scheduled route may be explicit in terms of locations and scheduled times, or may be a reference to a predefined route (e.g., a route number or service number) which is known by the entity executing the method. Said entity executing the method may receive the information from the sensor concerned, from a vehicle or vessel on which the sensor is mounted or from a still further actor, such as a public transport planner. Access to the information about the route allows the method to estimate the duration of this sensor's dwell time in the measuring zone, so that the method may prepare an assignment of sampling instances to apply after the sensor has left the measuring zone or may alternatively, if the remaining dwell time is to short, choose not assign sampling instants to other sensors with longer expected dwell times.

In a further development of this embodiment, a sensor or entity associated with the sensor creates the data representing the sensor's route by recording historic geolocations and discerning periodic patterns therein. This avoids any need to convert public transport timetables into routes represented in a computer-readable format, and the need to update the routes when timetables change.

In another further development of this embodiment, an assignment which is to apply after the sensor has left the measuring zone is prepared by associating a finite validity period with a sampling instant assigned to the sensor. The finite validity period may correspond to the remaining dwell time in the measuring zone, in view of the scheduled route of the sensor. Similarly, a second sensor which will succeed the leaving first sensor may be assigned a sampling instant that enters into force only when the first sensor is expected to have left the measuring zone. By assigning a set of sampling instants which changes deterministically with time, the number of necessary communication attempts with the mobile ambient sensors may be conveniently reduced.

In one embodiment, the sampling instants are assigned in view of a refractory period of each sensor. A refractory period (or recovery period) of a sensor is an amount of time which must elapse between two consecutive sampling instances of the sensor. A sensor may be associated with a non-zero refractory period as a result of its measuring principle (e.g., maximum readout frequency of photoelectric elements), downstream resources (e.g., throughput of signal processing circuitry) or a necessary adaptation to a new location to which it is moved (e.g., by allowing a measuring chamber time to purge and refill with ambient air). A sensor with a non-zero refractory period is normally unable of continuous operation at its nominal accuracy. According to this embodiment, the sampling instants are assigned in view of the refractory period. This may signify that the sampling instants must have a spacing greater than or equal to the refractory period.

In one embodiment, the sampling instants are assigned in view of a desired sampling periodicity. The sampling periodicity may represent a desired time separation of consecutive samples, independently of whether the samples are collected by one sensor or by an alternation of multiple sensors. A further development of this embodiment may take into account any known refractory period of the sensors; the sampling instants assigned to a sensor for which a refractory period applies must not be denser than the refractory period. If the refractory period is limiting to achieve a desired sampling periodicity, it may be necessary to involve more sensors, i.e., assign sampling instants to additional mobile ambient sensors present in the measuring zone.

In one embodiment, the mobile ambient sensors are configured to measure at least two different quantities, such as radio conditions and different aspects of air quality. Different sensors may be responsible for the different quantities, or each sensor may be multifunctional. According to this embodiment, the method accepts a definition of a measuring zone for each quantity independently. This allows a user to define a wider measuring zone for a quantity that is expected to have a slower spatial variation and vice versa.

It is understood that the method according to the first aspect may be performed at a controller, which has the authority to control the mobile ambient sensors directly or indirectly. As an example of indirect control, the controller may output an instruction needing to be forwarded to the sensors by a third party, such as an administrator. As a further example, the controller may be authorized to upload such instruction to the respective sensors, which however are configured to not execute the instruction unless an administrator transmits an authorization command to the sensors. The controller may be associated with one of the sensors (e.g., installed in a vehicle that carries one of the sensors) or may be centralized in the sense of not being associated with any sensor (e.g., host computer having a stationary location or installed in a vehicle not carrying any sensor). The controller may be entrusted with the further task of collecting data from the sensors and processing the data. If the method is performed by a controller associated with one of the mobile ambient sensors and the further sensors are associated with corresponding hardware, the performing controller may have been appointed by a leader election algorithm that is pre-agreed among the sensors.

A controller suitable for the above purposes may comprise a wireless interface for receiving a definition of a measuring zone and for detecting simultaneous presence of two or more mobile ambient sensors. The controller may further comprise processing circuitry configured to assign the sampling instants, which apply until a change in the simultaneous presence occurs.

The invention further relates to a computer program containing instructions for causing a computer, or the controller in particular, to carry out the above method. The computer program may be stored or distributed on a data carrier. As used herein, a "data carrier" may be a transitory data carrier, such as modulated electromagnetic or optical waves, or a non-transitory data carrier. Non-transitory data carriers include volatile and non-volatile memories, such as permanent and non-permanent storages of magnetic, optical or solid-state type. Still within the scope of "data carrier", such memories may be fixedly mounted or portable.

As used herein, a "location" may be geographical point or area, a road segment or a region of three-dimensional space. An "ambient sensor" is one configured to measure a physicochemical, optical, electromagnetic, biological or another location-dependent quantity. If such sensor is carried by a road or railroad vehicle, sea or air vessel or the like, then in normal circumstances the measured quantity is unrelated to the operation of the vehicle or vessel itself or only marginally perturbed by it (e.g., air quality sensor occasionally sensing vehicle's exhaust gases, cellular coverage sensor capturing reflections when metallic body parts align with base station antennas). Two or more ambient sensors carried by the same vehicle or vessel, which are therefore associated with identical routes, can nevertheless be treated independently in the present method, in particular as regards the assignment of sampling instants. For example, the sampling instants and sampling periodicity assigned to a one sensor need not coincide with those of a further sensor.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, on which.

DETAILED DESCRIPTION

The aspects of the present disclosure will now be described more fully hereinafter with reference to the accompanying drawings, on which certain embodiments of the invention are shown. These aspects may, however, be embodied in many different forms and the embodiments should not be construed as limiting; rather, they are provided by way of example so that this disclosure will be thorough and complete, and to fully convey the scope of all aspects of invention to those skilled in the art. Like numbers refer to like elements throughout the description.

Figure 1:
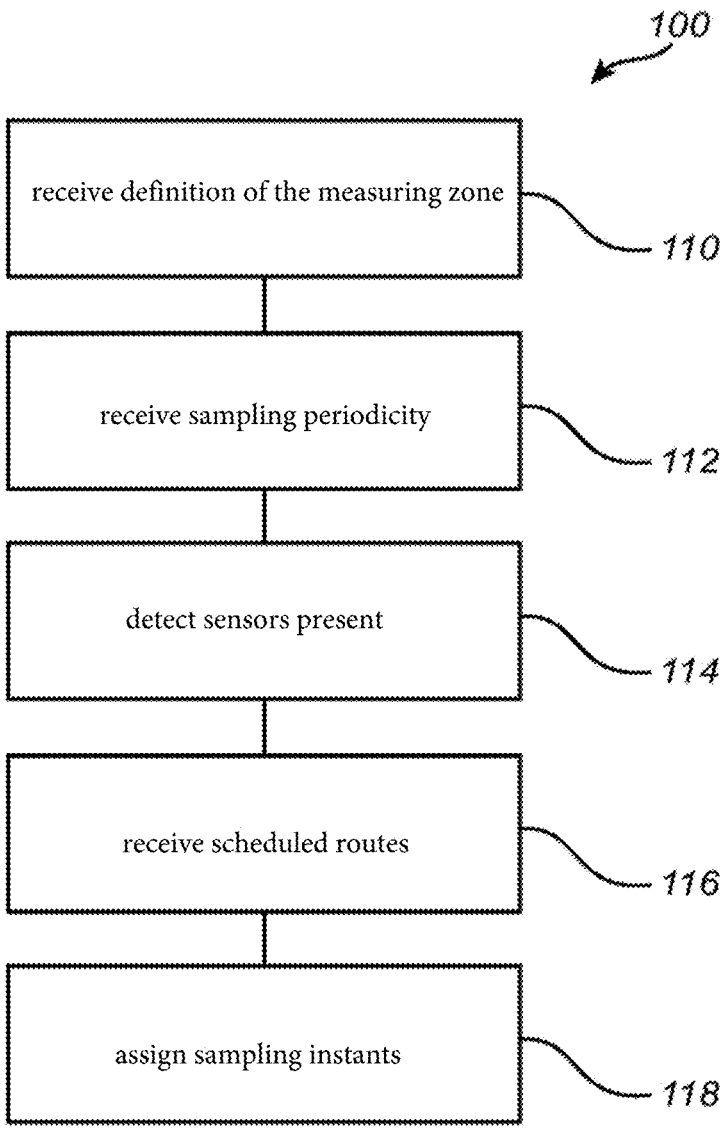
FIG. 1 is a flowchart of a method for coordinating sampling instants of a plurality of mobile ambient sensors according to an embodiment of the invention.

FIG. 1 is a flowchart of a method 100 for coordinating sampling instants of a plurality of mobile ambient sensors according to an embodiment of the invention. In what follows, the method 100 will be described when implemented by a controller 320 of the general type shown in the right portion of FIG. 3.

Figure 3:
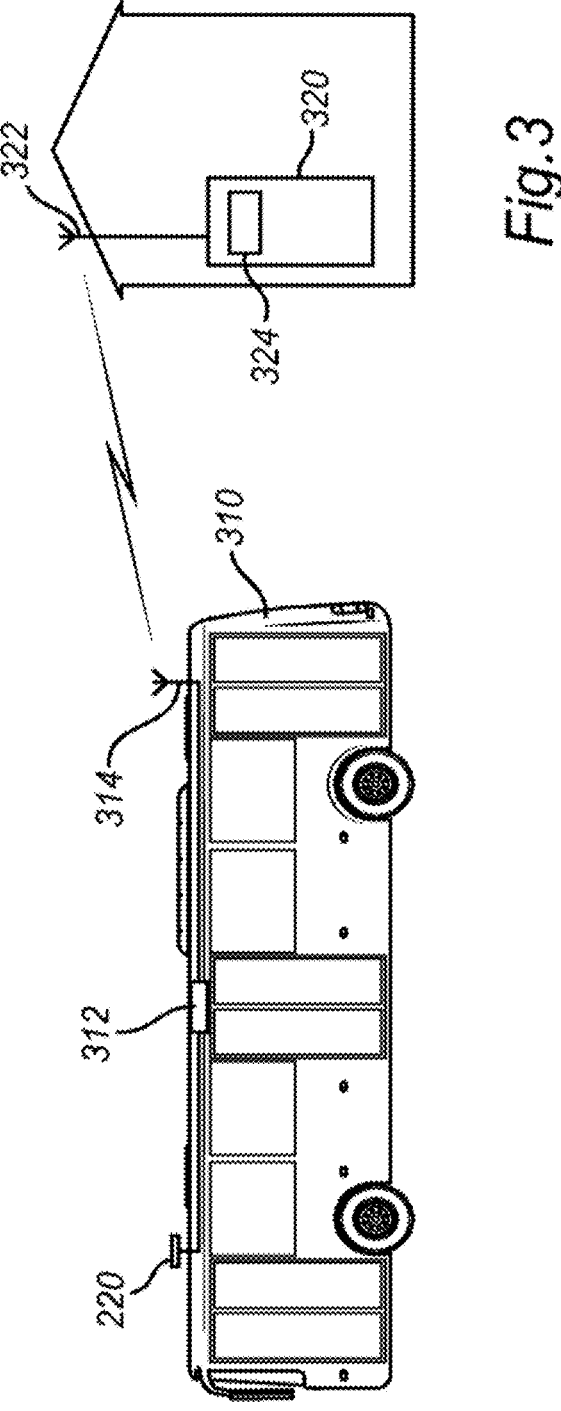
FIG. 3 shows a vehicle carrying two ambient sensors and is in wireless communication with a stationary controller.

The controller 320 may be a programmable general-purpose computer equipped with or connected to a communication interface towards the ambient sensors to be controlled. The controller 320 in this embodiment does not move with any of the ambient sensors during the execution of the method 100. In FIG. 3, it is shown located in a building. It is well known that a general-purpose computer includes memory, processing circuitry 324 and a data interface for inputting and outputting data. As shown in FIG. 3, the controller 320 further comprises a wireless interface 322 directly communicating with the ambient sensors. It is understood that the wireless interface 322 may equivalently be a connection to a cellular network, where the actual radio link to a sensor is established from a radio base station managed by a network operator. The wireless interface 322 is used for detecting the simultaneous presence of the ambient sensors. It may be used to inform the sensors of the sampling instants assigned to them, though this is not essential to allow execution of the method 100; the programming of the sensors in accordance with the method's 100 output data may be entrusted to another party.

Figure 2:
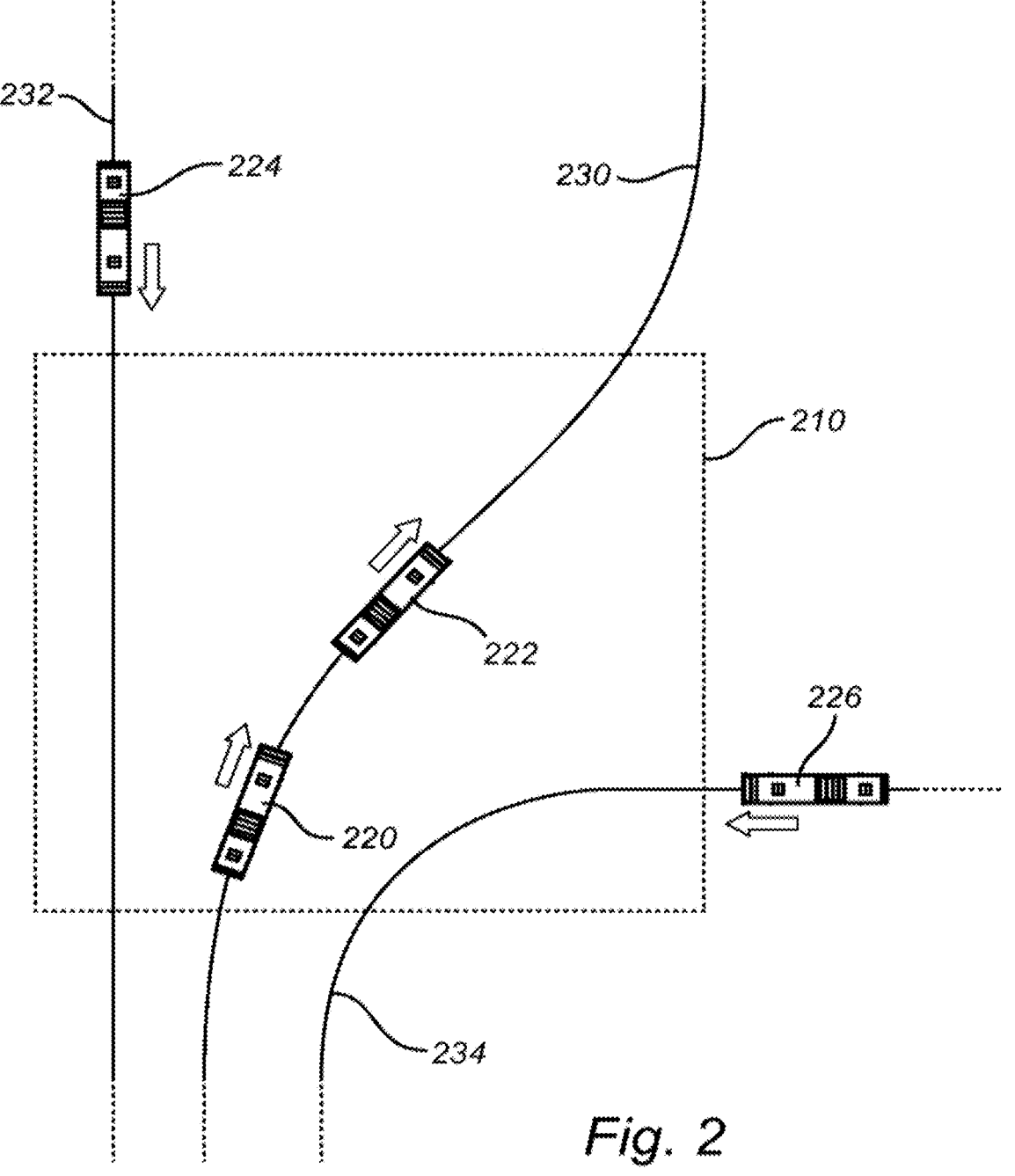
FIG. 2 is a schematic drawing of sensors moving along predefined routes which pass through a common measuring zone.

FIG. 2 illustrates a plurality of ambient sensors 220, 222, 224, 226.

While not essential to the invention, the sensors of this example move periodically along predefined routes. The periodical movement of the sensors may include repeated linear movement from an initial point to a final point, reciprocating movement (back and forth) between two endpoints, or cyclic movement along a closed curve. Here, sensors 220 and 222 move along a first route 230, sensor 224 moves along a second route 232, and sensor 226 moves along a third route 234. For clarity of the drawing, only portions of the first, second and third routes 230, 232, 234 are shown in FIG. 2. It is seen that all three routes 230, 232, 234 pass through a measuring zone 210, in which the first sensor 220 and second sensor 222 are currently present and into which the third sensor 224 and fourth sensor 226 are moving. Because a measurement in the measuring zone 210 can be effectuated by a freely selectable one of the sensors (when present), the method 100 has room to optimize the sampling instants.

Figure 4A:
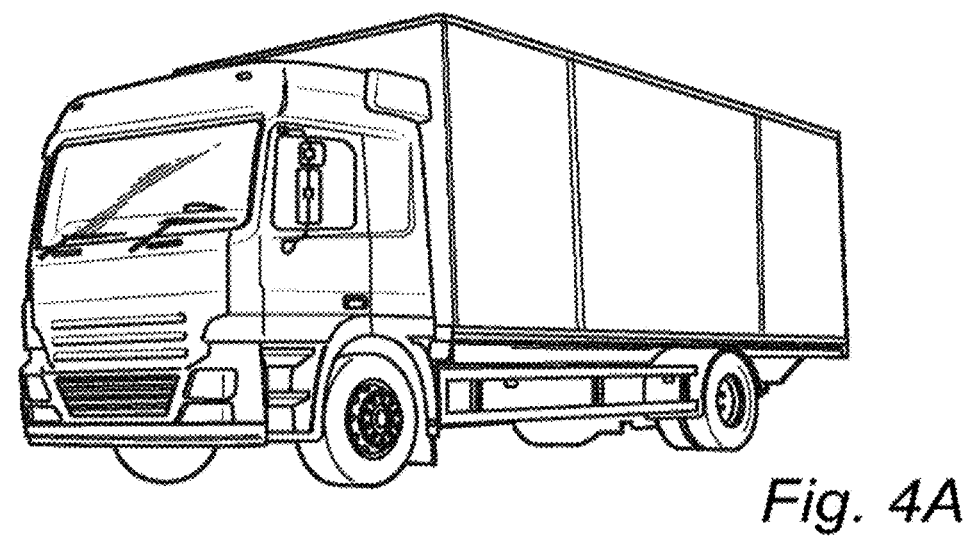
FIG. 4 shows example vehicles suitable for carrying mobile ambient sensors.
Figure 4B:
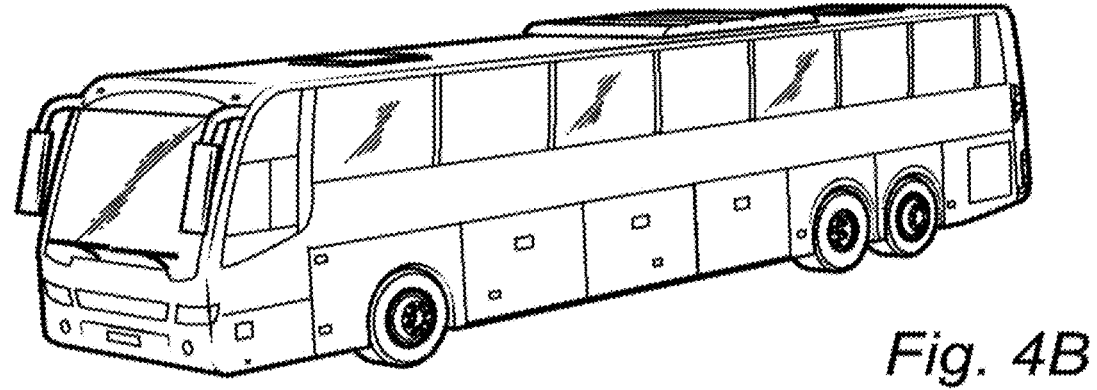
Figure 4C:
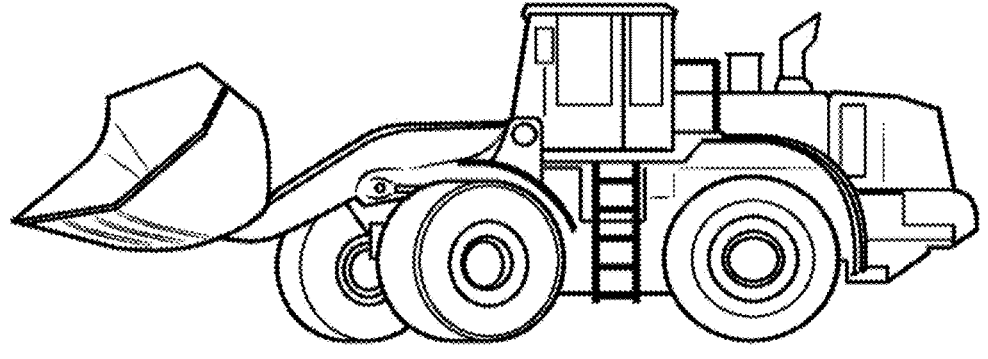

The sensors 220, 222, 224, 226 are mounted on vehicles, such as the truck, bus and construction equipment shown in FIG. 4. The vehicles may be conventional or autonomous (driverless). The vehicles are optionally geolocation-enabled. In general terms, "geolocation-enabled vehicles" includes vehicles and vessels with a Global Navigation Satellite Systems (GNSS) receiver, a cellular transceiver positionable in relation to base stations, a wireless local area network receiver positionable on the basis of a known access point location, an inertial measurement unit or other positioning equipment. Sensors which are associated with a positioning functionality are controllable on the basis of location. For example, each sensor may be configured to sample at assigned sampling instants until it receives a signal from the vehicle, on which it is mounted, that it is leaving the measuring zone 210. Alternatively, the sensor may receive updated geolocation data from the vehicle (or poll the vehicle for such data) and evaluate it against a received definition of the measuring zone 210. As a further alternative, the sensor may be geolocation-enabled in itself; at a possibly higher per-sensor cost, this avoids the reliance on the vehicle's positioning resources and the need to interface with these.

In the present example, the bus 310 shown in the left portion of FIG. 3 acts as the (geolocation-enabled) vehicle. The bus carries two sensors 220a, 220b which may for example be urban air quality sensors designed to measure nitrogen oxide pollutants (NOx) and particulate matter (PM), respectively. The sensors are connected to an internal controller 312 of the bus 310. The internal controller 312 serves as an interface towards resources shared by the bus 310, such as electric power, compressed air, a time signal, positioning services, data connectivity and the like. As suggested by an external antenna 314 in FIG. 3, the internal controller 312 can communicate with the controller 320 over its wireless interface 322.

The bus 310 is assumed to be a public transport vehicle serving a route defined in a public timetable, so that the sensors 220a, 220b will move periodically along this route. It is noted that many vehicle types operate according to non-public timetables or have periodic movement patterns for other reasons, which can therefore replace the bus 310 in this example. This includes refuse collection trucks, postal vehicles, street sweepers, mining and construction vehicles. However, as already explained, movement of sensors along scheduled routes—let alone periodic movement along scheduled routes—is not an essential feature of the invention.

Referring to a first step 110 of the method 100, a definition of the measuring zone 210 is received. The measuring zone 210 may be expressed directly as a polygon of geocoordinates, as a center point with a proximity radius; alternatively, the measuring zone 210 may be expressed indirectly in terms of a maximum attenuation of a reference signal from a radio transceiver (e.g., roadside unit) fixedly located in the measuring zone 210 or by reference to this transceiver's ability to receive a reference signal with a pre-agreed transmit power from a moving ambient sensor.

In a second step 112, a desired sampling periodicity is received. The sampling periodicity is ⅛ of a time unit. Equivalently, a sampling frequency is 8 samples per time unit.

In a next step 114, it is detected that currently, at time $t=T_1$ (see FIG. 5), the first sensor 220 and second sensor 222 are simultaneously present in the measuring zone 210. The detection may be based on a relative positioning procedure among the sensors, a geolocation procedure at one of the sensors, on a report received from a fixedly located radio transceiver in the measuring zone 210, or in accordance with the further options discussed above.

The method 100 moves on to a next step 116, where the information about the scheduled routes 230, 232, 234 of the sensors 220, 222, 224, 226 is received. It is derivable from the received information that in about one time unit, at $t=T_2$, the third sensor 224 and fourth sensor 226 will enter the measuring zone 210, so that four sensors are available to achieve the desired sampling periodicity ⅛. Optionally, the expected entry of the third sensor 224 and fourth sensor 226 may be verified by initiating an actual positioning process at or slightly after $t=T_2$. From the scheduled routes, it is furthermore derivable that the second sensor 222 will leave the measuring zone 210 at approximately $t=T_3$ and that the new simultaneous presence of three sensors will remain valid for approximately one time unit. This condition ends a time $t=T_4$, which may therefore be said to constitute the planning horizon of the method 100. Sampling instants after this point will be assigned in a next iteration.

In a step 118, sampling instants are assigned to the sensors. In the present embodiment, the assigned sampling instants have a finite validity period chosen from a partition of the planning horizon in view of the expected changes in simultaneous presence of the mobile ambient sensors. At time $t=T_1$, the partition may be chosen as $[T_1, T_2], [T_2, T_3], [T_3, T_4]$. A sensor is assigned a sampling instant valid in an interval $[T_n, T_{n+1}]$ only if the sensor is expected to be present in the measuring zone 210 then.

Figure 5:
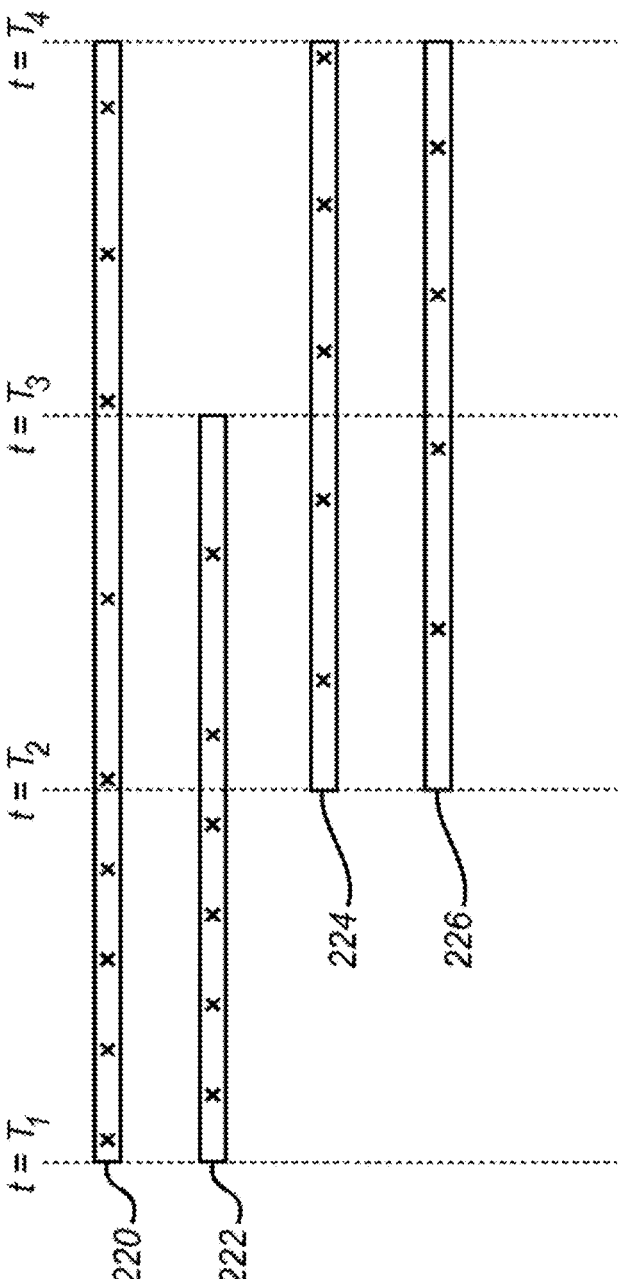
FIG. 5 illustrates sampling instants assigned to four sensors which are temporarily present in a measuring zone.

A possible outcome of the assigning step 118 is illustrated in FIG. 5. It is seen that the desired sampling periodicity of ⅛ time unit is achieved in $[T_1, T_2]$ by alternation of the first sensor 220 and second sensor 222, so that the sampling instants of each sensor are spaced by approximately ¼ time unit. The sampling periodicity is achieved in $[T_2, T_3]$ by an alternation of all four sensors, and in $[T_3, T_4]$ by an alternation of the first, third and fourth sensors 220, 224, 226. The sampling instants, illustrated by crosses x in FIG.

5, are distributed among the simultaneously present sensors in a rotating (or round-robin) fashion. This may be advantageous from the point of view of allowing sufficient recovery time; a tentative assignment of sampling instants may furthermore be verified for compliance with known refractory periods of the sensors before the assignment is made final and forwarded to the sensors. As an alternative to rotation, the sampling instants may be distributed in a quasi-random fashion, such as by ordering the sensors in accordance with their device identity numbers or a similar identifier.

It is noted that the sampling instants of the first sensor 220 are more precisely assigned to either the sensor 220a or the sensor 220b. Certainly these are carried by the same vehicle 310 but are treated as separate sensors for the purposes of this method 100. This is all the more justified if the sensors 220a, 200b are configured to measure different quantities.

The assigned sampling instants may be transmitted to the sensors 220, 222, 224, 226 as instructions in one of the ways outlined above. A main aspect to settle is whether the sampling instants are to be expressed on a one-off or periodic basis. A further aspect is whether the sampling instants shall refer to a known time base (synchronous system time) or to the time of receipt at each sensor. The second option of referring to a receipt time may be advantageous if a reliable wireless link to each sensor is available and the controller's 320 communication and processing capacity is sufficient to instruct the sensors in real time.

As time passes, it may be necessary to repeat the method 100, and in particular steps 114 and 188, so that measurements may continue in a coordinated fashion past the initial planning horizon $t=T_4$. The repetition may as well be triggered by a detected change in the simultaneous presence in the measuring zone 210.

In an optional further step of the method 100, the sampled measurements are received from the sensors 220, 222, 224, 226 and processed. The beneficiary of the measurements may be a telecommunications operator, an environment analyst or other stakeholder with an interest in the measuring zone 210.

In a variation of the described embodiment, the method 100 is executed by the internal controller 312 associated with sensors 220a, 220b. The beneficiary of the collected data may then be the vehicle 310 or a person using or traveling with the vehicle 310. The internal controller 312 may be elected as lead controller by the execution of a leader election algorithm by the simultaneously present sensors associated with analogous controller equipment; the leader election algorithm may be random or pseudo-random. When the method 100 is executed from an internal controller 312 of a vehicle, communication with other sensors (possibly, through the intermediary of the vehicles on which they are mounted) may proceed over a cellular network or short-range wireless. Multi-hop or 'meshed' communication, by which a nearby vehicle relays a message towards a more distant vehicle, is a way to alleviate the coverage limitations of short-range wireless, so as to increase the workable size of a measuring zone.

While clearly not essential to the method 100, some heuristics and automated approaches for assigning the sampling instants on the basis of a measuring zone—and possibly in view of any desired sampling periodicity and any refractory periods to be observed—will now be discussed. One possible approach is to perform a random or pseudo-random assignment of sampling instants, which is evaluated against predefined criteria and repeated if needed. The criteria may include:

completeness of time coverage, avoidance of clustering, observance of refractory periods, resilience (e.g., the number of independent sensors that are engaged to cover the measuring zone).

Another possible approach is to formulate an optimization problem which is solved numerically, with the sampling instants as output. The above criteria may either be included in an objective function or in boundary conditions. For example, the objective function may be dependent on the sampling instants and may include terms penalizing clustering and rewarding complete time coverage. The refractory periods, which are arguably of a more coercive character, may be included as boundary conditions. The objective function of such an optimization problem may further include a term rewarding the total number of samples collected, so as to reflect a desire to optimize the use of a given number of simultaneously present sensors. The choice of the numerical solver is not essential to the present invention; it will be within the skilled person's abilities to select a suitable one of the solvers described in the literature.

Machine learning methods constitute a still further option for automating the step 114 of detecting a simultaneous presence and/or the step 118 of assigning the sampling instants.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method of coordinating sampling instants of a plurality of mobile ambient sensors, which method is performed by a controller equipped with or connected to a communication interface with the mobile ambient sensors and comprises:

receiving a definition of a measuring zone;

detecting simultaneous presence of two or more mobile ambient sensors of the a plurality of mobile ambient sensors in the measuring zone, wherein the detection of said simultaneous presence is based on a relative positioning procedure among the plurality of mobile ambient sensors, a geolocation procedure performed at one of the plurality of mobile ambient sensors, a report received from a fixedly located radio transceiver in the measuring zone, or one or more measurement reports received by the controller from two or more mobile ambient sensors in the measuring zone;

assigning sampling instants to each of said two or more mobile ambient sensors, wherein the assigned sampling instants apply until a change in said simultaneous presence is detected;

operating the two or more mobile ambient sensors based on the assigned sampling instants.

2. The method of claim 1, further comprising detecting a change in said simultaneous presence by one of:

initiating a relative positioning procedure among the plurality of mobile ambient sensors;

initiating a geolocation procedure at one of the plurality of mobile ambient sensors;

receiving a report that one of the plurality of mobile ambient sensors is leaving or has left the measuring zone;

noting an absence of measurement report expected to be received by the controller from one of the sensors;

detecting a further simultaneously present sensor in the measuring zone.

3. The method of claim 1, wherein the assigned sampling instants are periodic sampling instants.

4. The method of claim 1, further comprising:

receiving information about a scheduled route of one of the simultaneously present sensors, wherein the assigning of sampling instants is performed in view of the scheduled route.

5. The method of claim 4, further comprising associating the assigned sampling instants with a finite validity period.

6. The method of claim 1, wherein:

each of the plurality of mobile ambient sensors is associated with a predefined refractory period, which must elapse between two consecutive sampling instants, the assigning of sampling instants is performed in view of the refractory period.

7. The method of claim 1, further comprising:

receiving a desired sampling periodicity, wherein said assigning includes ensuring that sampling instants assigned to different ones of the plurality of mobile ambient sensors are spaced in approximate agreement with the desired sampling periodicity.

8. The method of claim 1, wherein the plurality of mobile ambient sensors are configured to measure at least two different quantities, the method comprising:

receiving the definition of the measuring zone for each of the quantities.

9. The method of claim 1, wherein the method is performed by a controller associated with one of the simultaneously present sensors.

10. The method of claim 1, wherein the method is performed by a controller implemented by a host computer not associated with any sensor.

11. The method of claim 1, wherein the plurality of mobile ambient sensors are vehicle-mounted.

12. A controller operable to coordinate sampling instants of a plurality of mobile ambient sensors, which method is performed by a controller equipped with or connected to a communication interface with the mobile ambient sensors and the controller comprises:

a wireless interface configured to:

receive a definition of a measuring zone; and detect simultaneous presence of two or more mobile ambient sensors in the measuring zone, wherein the detection of said simultaneous presence is based on a relative positioning procedure among the two or more mobile ambient sensors, a geolocation procedure performed at one of the two or more mobile ambient sensors, a report received from a fixedly located radio transceiver in the measuring zone, or one or more measurement reports received by the controller from two or more mobile ambient sensors in the measuring zone, processing circuitry configured to:

assign sampling instants to each of said two or more mobile ambient sensors wherein the assigned sampling instants apply until a change in said simultaneous presence is detected; and operate the two or more mobile ambient sensors based on the assigned sampling instants.

13. A non-transitory computer readable medium storing a computer program comprising instructions to cause a controller to perform the method of claim 1.

14. The method of claim 1, wherein the measuring zone is user-defined.

15. The method of claim 1, wherein the measuring zone has such size that two measurements in the zone are mutually substitutable.

* * * * *